United States Patent
Witowski et al.

(10) Patent No.: US 11,957,412 B2
(45) Date of Patent: Apr. 16, 2024

(54) IMAGING DEVICE FOR OPHTHALMIC LASER SYSTEM USING OFF-AXIS MINIATURE CAMERA

(71) Applicant: AMO Development, LLC, Irvine, CA (US)

(72) Inventors: Zenon Witowski, Pleasanton, CA (US); Mohammad Saidur Rahaman, Santa Clara, CA (US); Daryl Wong, San Jose, CA (US)

(73) Assignee: AMO Development, LLC, Irvine, CA (US)

( * ) Notice: Subject to any disclaimer, the term of this patent is extended or adjusted under 35 U.S.C. 154(b) by 391 days.

(21) Appl. No.: 17/057,105

(22) PCT Filed: Nov. 11, 2019

(86) PCT No.: PCT/IB2019/059669
§ 371 (c)(1),
(2) Date: Nov. 20, 2020

(87) PCT Pub. No.: WO2020/109899
PCT Pub. Date: Jun. 4, 2020

(65) Prior Publication Data
US 2021/0275017 A1    Sep. 9, 2021

Related U.S. Application Data

(60) Provisional application No. 62/772,566, filed on Nov. 28, 2018.

(51) Int. Cl.
*A61B 3/14* (2006.01)
*A61B 3/00* (2006.01)
*A61F 9/008* (2006.01)

(52) U.S. Cl.
CPC ............ *A61B 3/145* (2013.01); *A61B 3/0008* (2013.01); *A61F 9/008* (2013.01); *A61F 2009/00897* (2013.01)

(58) Field of Classification Search
CPC ......... A61B 3/145; A61B 3/0008; A61B 3/14; A61F 9/008; A61F 2009/00897; A61F 9/00836; A61F 9/00827; A61F 9/009
(Continued)

(56) References Cited

U.S. PATENT DOCUMENTS

| 4,881,808 A | 11/1989 | Bille et al. |
| 5,640,962 A | 6/1997 | Jean et al. |

(Continued)

FOREIGN PATENT DOCUMENTS

| AU | 2009231687 A1 | 10/2009 |
| DE | 102004025999 A1 | 12/2005 |

(Continued)

OTHER PUBLICATIONS

International Search Report and written opinion for Application No. PCT/IB2019/059669, dated Feb. 6, 2020, 5 pages.

*Primary Examiner* — Mohammed A Hasan
(74) *Attorney, Agent, or Firm* — Johnson & Johnson Surgical Vision, Inc.

(57) ABSTRACT

An imaging system for an ophthalmic laser system includes a prism cone made of a transparent optical material and disposed downstream of the focusing objective lens of the ophthalmic laser system, the prism cone having an upper surface, a lower surface parallel to the upper surface, a tapered side surface between the upper and lower surfaces, and a beveled surface formed at an upper edge of the prism cone and intersecting the upper surface and the side surface, and a camera disposed adjacent to the prism cone and facing the beveled surface. The camera is disposed to directly (Continued)

receive light that enters the lower surface of the prism cone and exits the beveled surface without having been reflected by any surface.

11 Claims, 3 Drawing Sheets

(58) Field of Classification Search
USPC .......................................................... 351/206
See application file for complete search history.

(56) References Cited

U.S. PATENT DOCUMENTS

| | | | |
|---|---|---|---|
| 8,077,914 B1 * | 12/2011 | Kaplan | A61B 3/113 382/103 |
| 8,556,425 B2 | 10/2013 | Frey et al. | |
| 8,740,890 B2 | 6/2014 | Vogler | |
| 9,492,322 B2 * | 11/2016 | Goldshleger | A61F 9/008 |
| 2009/0247998 A1 * | 10/2009 | Watanabe | A61F 9/00827 606/5 |
| 2010/0324542 A1 * | 12/2010 | Kurtz | A61F 9/00825 606/6 |
| 2013/0070203 A1 | 3/2013 | Michaels et al. | |
| 2013/0102922 A1 | 4/2013 | Gooding et al. | |
| 2014/0276678 A1 | 9/2014 | Berry et al. | |
| 2016/0089270 A1 * | 3/2016 | Fu | A61F 9/0084 606/5 |
| 2020/0188166 A1 * | 6/2020 | Buck | A61F 9/008 |

FOREIGN PATENT DOCUMENTS

| | | |
|---|---|---|
| WO | 2011017018 A2 | 2/2011 |
| WO | 2016209312 A1 | 12/2016 |
| WO | 2018138552 A1 | 8/2018 |
| WO | 2019068869 A1 | 4/2019 |

* cited by examiner

IMAGING DEVICE FOR OPHTHALMIC LASER SYSTEM USING OFF-AXIS MINIATURE CAMERA

CROSS REFERENCE TO RELATED APPLICATIONS

This application is a U.S. national stage of and claims the benefit under 35 U. S.C. 371 of International Patent Application No. PCT/IB2019/059669, filed Nov. 11, 2019, which claims priority to, and the benefit of, under 35 U. S.C. § 119(e) of U. S. Provisional Appl. No. 62/772,566, filed Nov. 28, 2018, which are incorporated by reference in their entirety.

BACKGROUND OF THE INVENTION

Field of the Invention

This invention relates to an imaging system for an ophthalmic laser system, and in particular, it relates to such an imaging system using a miniature camera located off-axis of the laser beam.

Description of Related Art

In an ophthalmic laser system, a monitoring video camera is often provided to image the patient's eye before and during ophthalmic procedures to provide live monitoring. For example, cornea imaging during a femtosecond laser refractive procedure provides a powerful tool for doctors and users to monitor live refractive procedures. In some ophthalmic laser systems, the monitoring camera shares a portion of the optical path of the laser beam delivery optics of the laser system. This is referred to as an on-axis configuration. In such a system, light from the patient's eye that travels along the optical path of the treatment laser beam but in the opposite direction is collected and delivered to the monitoring camera. In some systems, a beam splitter is provided downstream (in the direction of the treatment laser beam) of the focusing objective of the laser beam delivery optics, to reflect the light from the eye to the monitoring camera. In some other systems, a beam splitter is located upstream of the focusing objective, to direct the light from the eye that has passed through the focusing objective to the monitoring camera.

SUMMARY

The present invention is directed to an imaging apparatus and related method for an ophthalmic laser system that substantially obviates one or more of the problems due to limitations and disadvantages of the related art.

Additional features and advantages of the invention will be set forth in the descriptions that follow and in part will be apparent from the description, or may be learned by practice of the invention. The objectives and other advantages of the invention will be realized and attained by the structure particularly pointed out in the written description and claims thereof as well as the appended drawings.

To achieve the above objects, the present invention provides an imaging system for an ophthalmic laser system, which includes: a prism cone made of a transparent optical material and disposed downstream of the focusing objective lens of the ophthalmic laser system, the prism cone having an upper surface, a lower surface parallel to the upper surface, a tapered side surface between the upper and lower surfaces, and a beveled surface formed at an upper edge of the prism cone and intersecting the upper surface and the side surface; and a camera disposed adjacent to the prism cone, the camera having an image detector that faces the beveled surface of the prism cone, wherein the camera is disposed to directly receive light that enters the lower surface of the prism cone and exits the beveled surface without having been reflected by any surface.

It is to be understood that both the foregoing general description and the following detailed description are exemplary and explanatory and are intended to provide further explanation of the invention as claimed.

DETAILED DESCRIPTION OF PREFERRED EMBODIMENTS

Embodiments of the present invention provide an imaging system for an ophthalmic laser system, which uses one or more miniature cameras in an off-axis configuration. In an off-axis configuration, the light from the patient's eye that travels in a direction non-parallel to the optical axis of the laser beam delivery optics is collected by the video camera. In one embodiment, the video camera is mounted at an off-axis location and its image detector faces toward the surface of the eye in an off-axis direction, and directly receives the light emitted or reflected from the eye without any reflecting mirror.

Figure 1:
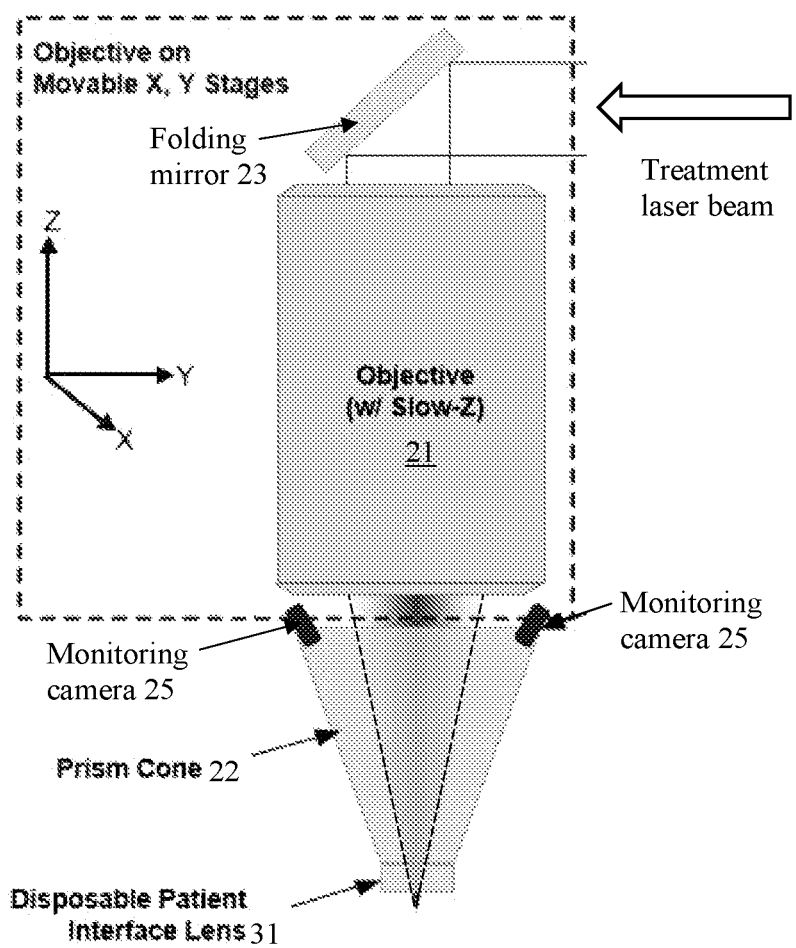
FIG. 1 schematically illustrates various optical components of a portion of an ophthalmic laser system which implements an off-axis imaging system according to an embodiment of the present invention.
Figure 2:
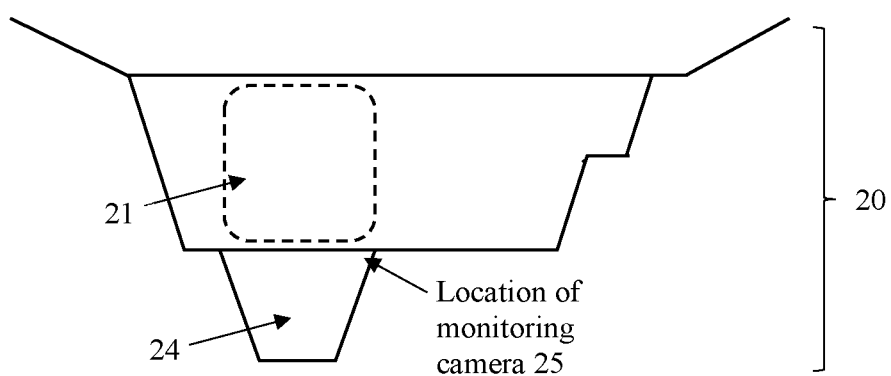
FIG. 2 schematically illustrates the exterior of a portion of the ophthalmic laser system which implements the off-axis imaging system according to the embodiment of the present invention.

FIGS. 1 and 2 schematically illustrate a portion 20 of an ophthalmic laser system which implements an off-axis imaging system according to embodiments of the present invention. FIG. 1 shows a number of components of the laser beam delivery optics, including an objective lens assembly 21 and a prism cone 22 disposed downstream of the objective lens. In the illustrated embodiment, the objective lens 21 is mounted on a moveable X-Y stage (not shown) and is also moveable along the Z direction, where the Z direction is parallel to the optical axis of the laser beam and the X and Y directions are orthogonal to Z. The prism cone 22 is a block of transparent optical material mounted in a truncated-cone shaped portion 24 (see FIG. 2, side view) of the housing of the laser beam delivery system. The block of optical material can effectively increase the focal length of the objective lens 21 without increasing the f number of the objective lens.

During ophthalmic procedures, a patient interface device is attached to the laser system around the truncated-cone shaped portion 24 of the housing, so that a disposable patient interface lens 31 is disposed directly below the lower (distal) end of the prism cone 22 (see FIG. 1). The patient interface lens 31 may be in contact with the lower surface of the prism cone 22. The patient's eye (not shown in the drawings) is mechanically engaged with the patient interface device and located directly below and in contact with the patient interface lens 31. In some embodiments, the diameters of lower surface of the prism cone 22 and the patient interface lens 31 are on the order of 10 mm.

In the embodiment illustrated in FIG. 1, a folding mirror 23 reflects the incoming treatment laser beam into the objective lens 21. The components of the laser system upstream of the folding mirror 23 may include (not shown in the drawings) a beam shaping aperture, a fast-z lens configured to scan the focus point of the laser beam in the z direction at a fast speed, a high frequency resonant scanner configured to scan the focus point along a scan line in the X-Y plane, a scan-line rotator configured to rotate the beam around the Z axis so as to rotate the direction of the scan line in the X-Y plane, a beam expander, and other lenses and mirrors. One laser system containing such components is described, for example, in commonly-owned U.S. patent application Ser. No. 14/865,396, filed Sep. 25, 2015, published as U.S. Pat. Appl. Pub. No. 2016/0089270, the disclosure of which is incorporated by reference in its entirety. The laser system may include other components, or may omit some of the components mentioned above.

Figure 3:
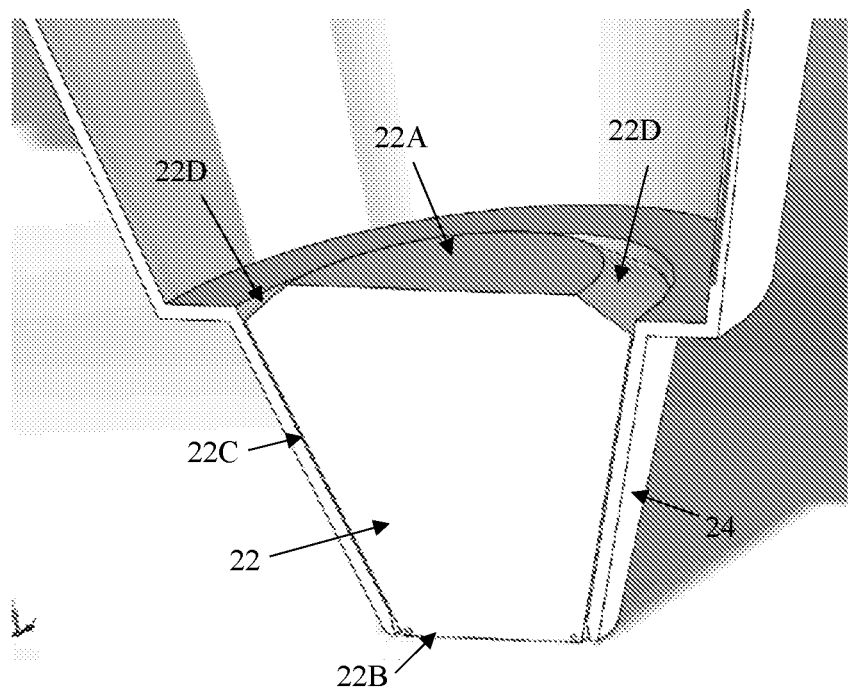
FIG. 3 is a perspective cut-away view of a part of the housing of the laser system and the prism cone adapted for mounting a miniature camera according an embodiment of the present invention.
Figure 4:
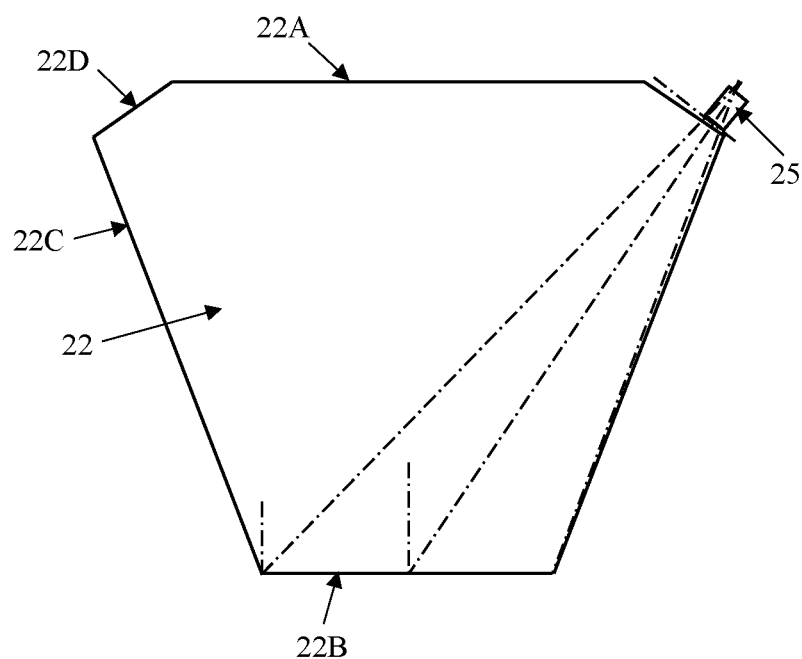
FIG. 4 is a side cross-sectional view of the prism cone and miniature camera according an embodiment of the present invention.

As shown in FIG. 1, one or two monitoring cameras 25 are mounted at or near the upper edge of the prism cone 22. FIG. 3 is a perspective cut-away view of a part of the housing 24 and the prism cone 22, and FIG. 4 is a schematic side cross-sectional view of the prism cone 22 with one mounted camera 25. As shown in FIGS. 3 and 4, the prism cone 22 has a round upper surface 22A, a round lower surface 22B parallel to the upper surface, and a tapered side surface 22C between the upper and lower surfaces. The lower surface 22B is smaller than the upper surface 22A, so the prism cone 22 has the general shape of a truncated cone. A circular beveled surface 22D is formed at the upper edge of the prism cone 22 and intersects the upper surface 22A and the side surface 22C. The camera 25 is mounted so that its image detector faces the circular beveled surface 22D. Light that enters the lower surface 22B can travel through the prism cone 22 to exit the beveled surface 22D and be received by the camera 25, without being reflected by any surface.

This way, the camera 25 will capture a view of the imaging plane, located at or below the lower surface 22B, during a procedure. During a procedure such as flap cutting or lenticule cutting in the cornea, or during diagnostic imaging, the patient interface lens 31 and the applanated cornea will be located at the imaging plane. At other times, such as during docking (when the patient interface device is being brought into engagement with the eye) or in vivo monitoring, other structures may be viewed at the imaging plane.

In some embodiments, the physical size of the camera 25 face that faces the prism cone 22 is on the order of 1 mm×1 mm. An electrical cable or ribbon (not shown) extends from the back of the camera body to connect the camera to its control electronics (not shown). A lens is provided in front of the camera's image detector to form an image onto the detector. The lens may be integrated in the camera's body. Miniature cameras with a physical size on the order of 1 mm by 1 mm by a few mm, and a resolution of a few hundred pixels by a few hundred pixels, are available from various manufacturers. In one particular example, with a suitable lens in front of the detector, the camera can provide a field of view in air of approximately 90 degrees and a depth of view of approximately 3 to 50 mm.

As mentioned earlier, the prism cone 22 is a block of optical material, which functions to effectively increase the focal length of the objective lens 21 without increasing the f number of the objective lens. Some examples of suitable optical materials for the prism cone include: fused silica (FS), which has a refractive index of n=1.45 at wavelength of 1 μm; lanthanum flint (LaF), n=1.73 at 1 μm; and lanthanum dense flint (LaSF), n=1.98 at 1 μm.

The camera 25 may be attached to the prism cone 22 by a suitable transparent adhesive. Preferably, the adhesive is an index matching adhesive having a refractive index approximately equal to (e.g., within ±0.1) that of the optical material of the prism cone 22. One example of a suitable index matching adhesive is NOA 146H manufactured by Norland Products, which has a refractive index of 1.46, close to that of fused silica. This adhesive is a clear, colorless, liquid photopolymer that will cure when exposed to ultraviolet light and/or heat.

Figure 5:
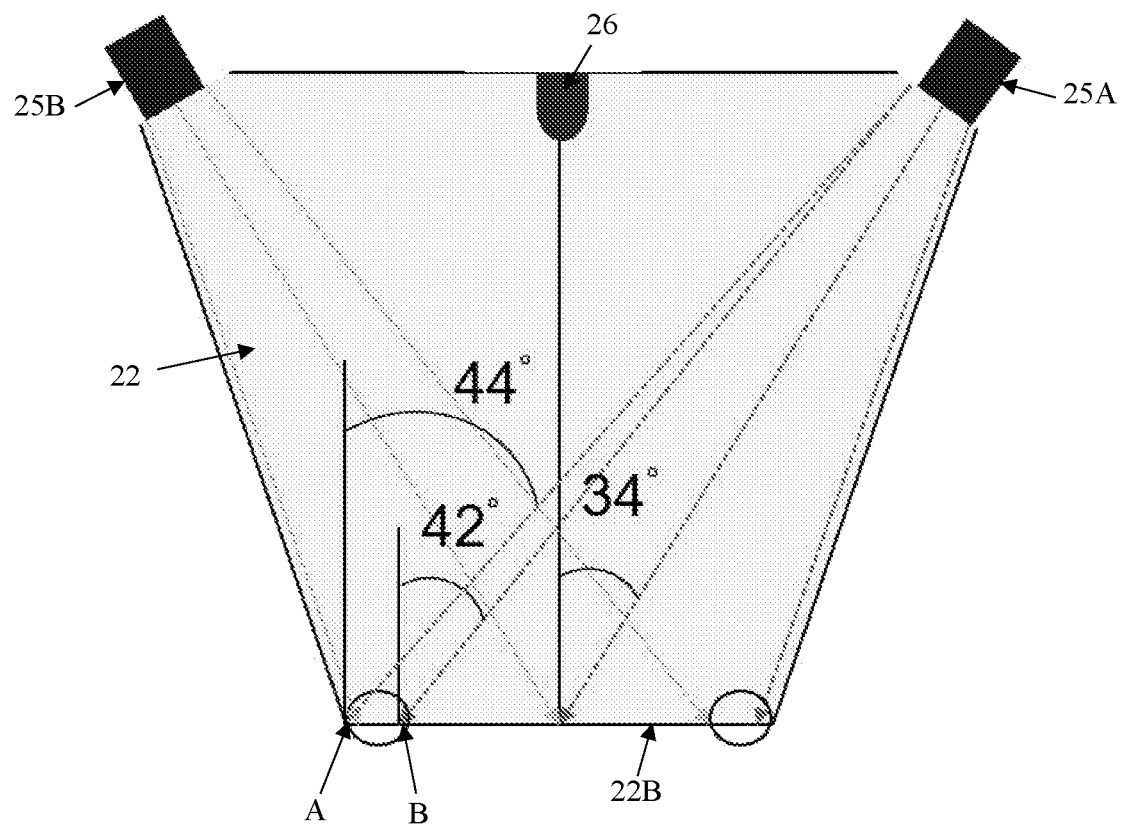
FIG. 5 schematically illustrates an example of limited field of view of a camera due to high refractive index of the prism cone.

Depending on the optical material and geometry of the prism cone 22, a single camera 25 may not be able to image the entire target field of view (FoV), i.e., the entire area of the lower surface 22B of the prism cone 22. When the refractive index $n_2$ of the optical medium below the lower surface 22B (e.g., air) is lower than the refractive index $n_1$ of the optical material of the prism cone, the propagation angle of any light that has entered the prism cone through the interface 22B cannot be greater than the critical angle $\theta_c = \arcsin(n_2/n_1)$. Here, the propagation angle is defined with respect to the normal direction of the interface 22B. As illustrated in FIG. 5, this may limit the area of the interface 22B that can be imaged by the camera 25.

In the particular example schematically shown FIG. 5, the medium below the prism cone 22 is air and the optical material of the prism cone is BK7 optical glass with a refractive index of 1.50, which gives a critical angle $\theta_c$ of approximately 42°. In this example, the prism cone is shaped such that at a point A on the edge of the lower surface 22B, the angle from point A to the camera 25A is approximately 44°. At a point B of the lower surface 22B located between the edge and the center, the angle from point B to the camera 25A is approximately 42° (the critical angle). Because the light entering the interface 22B from the medium below must have a propagation angle less than the critical angle 42° as discussed above, the light entering through the area between point A and point B cannot reach the camera 25A, so this area cannot be imaged by the camera 25A. Note that for this given geometry, if an optical material of higher refractive index is used, the area that cannot be imaged by a single camera 25A will be even larger.

Figure 6:
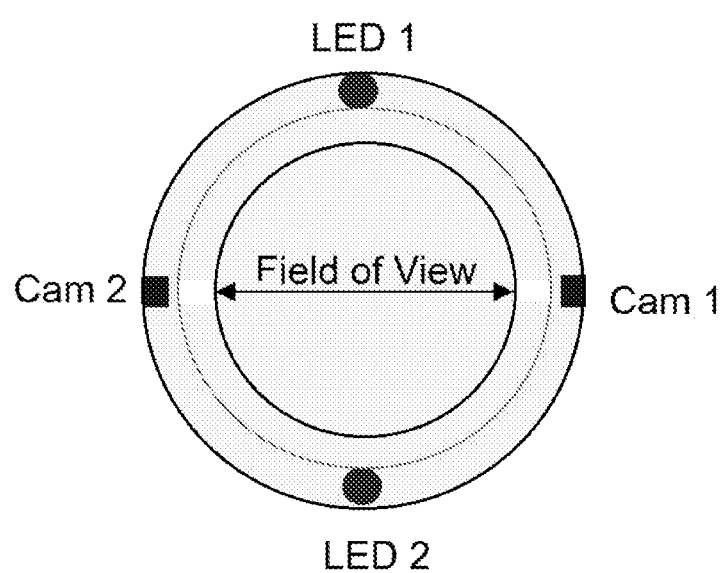
FIG. 6 illustrates a top view of a prism cone with two cameras and two illumination lights according an embodiment of the present invention.

In such a situation, two or more cameras may be used to ensure that the entire area of the lower surface 22B can be imaged. In the example shown in FIGS. 5 and 6, two cameras 25A and are provided at diametrically opposed positions along the circular beveled surface 22D. As can be seen in FIG. 5, the area AB not imaged by camera 25A can be imaged by camera 25B. Similarly, a symmetrically located area not imaged by camera 25B can be imaged by camera 25A.

An illumination source (e.g. light emitting diode or LED) 26 is also shown in FIG. 5. The LED may be mounted on the circular beveled surface 22D or mounted on the housing 24 and facing the beveled surface 22D. In one embodiment, two LEDs are provided, each located along the circular beveled surface 22D halfway between the two cameras (see FIG. 6, top view). This configuration can avoid direct reflection of the illumination light by the interface 22B into the cameras. When only one camera and one LED are provided, the LED may be provided at a 90 degree angle or another suitable distance from the camera to avoid direct reflection of the illumination light into the camera. Other numbers of cameras and LEDs may also be used.

Note that while the prism cone 22 in the illustrated embodiment has the general shape of a truncated cone (i.e. with a tapered side surface), this is not a requirement. The block of optical material may alternatively have the general shape of a straight cylinder, i.e. with a vertical side surface. Such a cylindrical block of material can also accomplish the purpose of effectively extending the focal length of the objective lens. However, when the size of the objective lens is larger than the size of the patient interface lens, a truncated-cone shaped block is more practical. In addition, the upper and lower surfaces are not required to have round shapes, although round shapes are again more practical.

Also note that while in the illustrated embodiment the beveled surface 22D extends around the entire upper edge of the prism cone (see FIG. 3), this is not necessary. Rather, the beveled surface may consist of several isolated beveled surface patches along the upper edge of the prism cone, each of which intersecting the upper and side surfaces and providing a mounting site for a camera or an LED.

The off-axis cornea imaging system described above can provide sufficient resolution to reveal an entire dissection plane of the cornea structure. This can realize an accurate live monitoring of the entire surgical plane during an ophthalmic procedure and diagnosis. It will allow the surgeon and/or other user to assess the progression of the procedure in real time and evaluate any associated surgical events.

The imaging system can be accomplished without significant modification to the laser beam delivery system. For example, it does not require any modification of either the focusing lens 21 and components upstream of the lens, or the prism cone 22, or the truncated-cone shaped housing portion 24.

Moreover, because the monitoring cameras are located near the upper end of the prism cone, the imaging system does not occupy any space around the side of the truncated-cone shaped portion 24 of the laser system housing. Further, as mentioned earlier, the prism cone of high refractive index material increases the focal length of the objective lens, which allows for a longer space between the objective lens and the eye. Providing a longer space between the objective lens and the eye and keeping the entire space around the truncated-cone shaped portion 24 clear are advantageous for the purpose of allowing the surgeon a clear line of sight to the eye and more room to manipulate the patient interface device during the docking process. This is important because the upper delivery platform, located in the portions of the exterior housing above the truncated-cone shaped portion 24, tend to be wide and bulky.

It will be apparent to those skilled in the art that various modification and variations can be made in the imaging system for ophthalmic laser system and related method of the present invention without departing from the spirit or scope of the invention. Thus, it is intended that the present invention cover modifications and variations that come within the scope of the appended claims and their equivalents.

What is claimed is:

1. An imaging system for an ophthalmic laser system, the ophthalmic laser system comprising a focusing objective lens, the imaging system comprising:
   a prism cone made of a transparent optical material and disposed downstream of the focusing objective lens, the prism cone having an upper surface, a lower surface parallel to the upper surface, a side surface between the upper and lower surfaces, and a beveled surface formed at an upper edge of the prism cone and intersecting the upper surface and the side surface, wherein the upper surface and the lower surface intersect an optical axis of the objective lens; and
   a camera disposed adjacent to the prism cone, the camera having an image detector that faces the beveled surface of the prism cone, wherein the camera is disposed to directly receive light that enters the lower surface of the prism cone and exits the beveled surface without having been reflected by any surface.

2. The imaging system of claim 1, wherein the upper surface has a round shape, the lower surface has a round shape, and the lower surface is smaller than the upper surface.

3. The imaging system of claim 1, wherein the beveled surface extends around an entirety of the upper surface.

4. The imaging system of claim 1, further comprising a transparent adhesive for attaching the camera to the beveled surface.

5. The imaging system of claim 4, wherein the adhesive has a refractive index approximately equal to that of the transparent optical material of the prism cone.

6. The imaging system of claim 1, further comprising an illumination light disposed adjacent the prism cone and facing the beveled surface.

7. The imaging system of claim 1, wherein the camera is a first camera, the system further comprising a second camera disposed adjacent to the prism cone, the second camera having an image detector that faces the beveled surface of the prism cone, the first camera and the second camera being disposed at diametrically opposed positions.

8. The imaging system of claim 7, further comprising two illumination light disposed adjacent the prism cone and facing the beveled surface, each illumination light being disposed halfway between the first and second cameras.

9. The imaging system of claim 8, wherein the beveled surface includes four isolated beveled surface patches each formed at the upper edge of the prism cone and intersecting the upper and side surfaces, wherein the first and second cameras and the two LEDs each corresponds to one of the beveled surface patches.

10. The imaging system of claim 1, further comprising a truncated-cone shaped housing, wherein the prism cone is disposed in the housing.

11. The imaging system of claim 1, wherein the side surface is tapered.

* * * * *